United States Patent
Inaba

(10) Patent No.: US 8,814,837 B2
(45) Date of Patent: Aug. 26, 2014

(54) SIMPLE DEVICE FOR TREATING TINEA UNGUIUM

(76) Inventor: Yoichi Inaba, Kumamoto (JP)

( * ) Notice: Subject to any disclaimer, the term of this patent is extended or adjusted under 35 U.S.C. 154(b) by 688 days.

(21) Appl. No.: 13/127,492

(22) PCT Filed: Nov. 2, 2009

(86) PCT No.: PCT/JP2009/005808
§ 371 (c)(1),
(2), (4) Date: May 4, 2011

(87) PCT Pub. No.: WO2010/055622
PCT Pub. Date: May 20, 2010

(65) Prior Publication Data
US 2011/0245785 A1    Oct. 6, 2011

(30) Foreign Application Priority Data

Nov. 17, 2008  (JP) ................. 2008-292958
Apr. 27, 2009  (JP) ................. 2009-107244
Sep. 7, 2009   (JP) ................. 2009-205412

(51) Int. Cl.
*A61F 13/00* (2006.01)
*A61K 9/08* (2006.01)
*A61K 31/137* (2006.01)
*A61K 9/00* (2006.01)

(52) U.S. Cl.
CPC ............. *A61M 35/006* (2013.01); *A61K 9/08* (2013.01); *A61K 31/137* (2013.01); *A61K 9/0014* (2013.01)
USPC ............. 604/304; 604/289; 604/290; 424/61; 424/443

(58) Field of Classification Search
CPC ..... A61M 1/00; A61M 1/0058; A61M 1/008; A61M 1/0088; A61M 27/00; A61M 35/00; A61M 37/0015; A61F 13/06; A61F 13/068; A61F 13/10; A61F 13/8405
USPC ................. 604/304, 305; 424/61, 78.3, 445
See application file for complete search history.

(56) References Cited

U.S. PATENT DOCUMENTS

| | | |
|---|---|---|
| 5,086,763 A | 2/1992 | Hathman |
| 6,623,457 B1 | 9/2003 | Rosenberg |
| 2002/0197094 A1 | 12/2002 | Gruenbacher et al. |
| 2003/0219469 A1 | 11/2003 | Johnson et al. |
| 2005/0058711 A1 | 3/2005 | Massengale et al. |
| 2006/0065677 A1 | 3/2006 | Py et al. |
| 2008/0306456 A1 | 12/2008 | Riesinger |

FOREIGN PATENT DOCUMENTS

| | | |
|---|---|---|
| EP | 1541111 A1 | 6/2005 |
| FR | 2359589 A1 | 2/1978 |
| FR | 2656218 A1 | 6/1991 |
| JP | 2003-126136 | 5/2003 |
| JP | 2004-135954 | 5/2004 |
| JP | 2006-075357 | 3/2006 |
| WO | 03097476 A1 | 11/2003 |

*Primary Examiner* — Melanie Hand
(74) *Attorney, Agent, or Firm* — Bacon & Thomas, PLC

(57) ABSTRACT

Provided is a device for treating *tinea* unguium which allows unrestricted treatment even for patients with basic diseases such as liver diseases, pregnant women and lactating patients and by which interindividual difference in the treatment can be avoided and antifungal agent for external use can be transdermally absorbed from the nail surface to the deep part of the nail economically, safely and efficiently within a short period of time without any side effects. A dome-shaped applicator, which is formed of a flexible material, which has an open part provided with a flange for adhesion and which is formed to have a larger film thickness in the periphery adjacent to the open part than the film thickness in other parts, is hermetically bonded to a surface of a nail. Then, the liquid antifungal agent for external use is fed into the dome-shaped applicator under pressure using an injector and is allowed to be efficiently penetrated into the deep part of the nail using positive pressure.

5 Claims, 18 Drawing Sheets

SIMPLE DEVICE FOR TREATING TINEA UNGUIUM

TECHNICAL FIELD

The present invention relates to a device for treating a nail infected with *Trichophyton*. More particularly, the present invention is directed to a simple device for treating *tinea unguium* that has a dome-shaped applicator adapted to be filled with a liquid antifungal agent for external use and configured to be hermetically bonded to a surface of a *Trichophyton*-infected nail so that the antifungal agent for external use is efficiently impregnated deep into the *Trichophyton*-infected nail.

BACKGROUND ART

For the treatment of *tinea* unguium of nail, generally hitherto adopted is a method in which a liquid antifungal agent for external use is applied to a surface of the nail or a method in which an antifungal agent is orally administered. An antifungal agent for external use does not penetrate into the nail unless it is dissolved in a solvent. The kind of a usable solvent is, however, restricted. Further, even a usable solvent is feasible, its efficiency is low because the solubility of the agent in the solvent is very low, namely about 2% at maximum.

Thus, mere application of a conventionally employed antifungal agent for external use to a surface of the nail cannot obtain sufficient effect of penetration thereof into the nail because the solvent is readily evaporated and, therefore, the viscosity thereof increases. A nail has a hard tissue composed of walls of bricks of keratin, which is a protein, and does not have sebaceous gland or sweat gland. Therefore, neither sweat nor sebum, which might act as the solvent, is secreted from the nail. Moreover, the nail has a three-layered structure in which the outermost surface layer is hard. When a liquid antifungal agent for external use dissolved in a solvent is applied to the nail, therefore, it takes a long time for the antifungal agent for external use to penetrate from the surface of the nail into a deep part thereof. During the course of the penetration, the solvent is evaporated so that it becomes more difficult for the antifungal agent to penetrate into the nail.

It is also known to use a dry-type tape, such as a transdermal absorbing tape, that is generally used in patients suffering from asthma or cardiopathy, for the treatment of *tinea* unguium. Because a suitable solvent for use in such a transdermal absorbing tape is not available, however, the antifungal agent is not maintained in a dissolved state and cannot be transferred to a deep part of the nail. A nail lacquer-type method is also known in which the property of a manicure coated on a nail that the surface of the coating dries first and the portion in contact with the nail dries last is utilized to cause an antifungal agent for external use contained therein to penetrate into the nail before the drying thereof is completed. An antifungal agent for external use that is suitable for such a method is also known. This method, however, is not very effective to cause the antifungal agent for external use to penetrate deep into the nail, because the solvent used therein rapidly evaporates. A further method is known in which a gauze impregnated with a liquid antifungal agent for external use is placed on a nail and a finger cot is then closely fitted over the entire finger. With this method, however, since the organic solvent and the antifungal agent for external use which are impregnated in the gauze are held for a long time in contact with a skin part other than nail, skin irritation is often caused.

In addition, since the conventional devices used in the foregoing methods are not of a completely sealing type, the solvent for the antifungal agent for external use may leak around the intended location. Therefore, it is not possible to precisely judge whether an effective amount of the antifungal agent for external use has penetrated into a deep part of the nail. This may cause a problem of variation in the treatment effect. As a substitute for the above methods for applying an antifungal agent for external use onto a surface of the nail, a method is proposed in which an oral antifungal agent is administered. However, since the absorbing rate of such a medicine is very low because of its inherent property, there is a case in which the antifungal agent is not at all transferred to the nail by administration depending upon cases. Thus, this method has a problem that a sufficient effect is not obtainable. Further, there is an interindividual difference in the effect of treatment of *tinea* unguium by an oral antifungal agent. Moreover, it is necessary to continue the treatment until the nail has been healed completely, i.e. generally for a period of as long as about one year. Therefore, this method has further problems that the treatment is not freely applicable to patients with basic diseases or pregnant women due to side effects of the medicine and treatment costs inevitably increase.

As a substitute for the aforementioned methods, there have been proposed the following devices that can permit an antifungal agent for external use to penetrate into a deep part of a nail:

a device for promoting penetration of an antifungal agent into a deep part of a nail, which has an ultrasonic wave generation element for directly irradiating an ultrasonic wave generated therefrom to an ultrasonic wave transmission medium disposed in contact with a surface of the nail to which a required amount of an antifungal agent for external use has been previously applied (Patent Document 1);

an athlete's foot treating apparatus including an electromagnetic wave oscillator for oscillating a gigahertz band electromagnetic wave and an emitting part for emitting the gigahertz band electromagnetic wave, wherein the emitting part is directed toward the affected area for irradiation thereof to heat sterilize *Trichophyton* in the horny layer and inside and back side of the nail (Patent Document 2); and an athlete's foot treating device including a container containing a liquid in which the affected area is to be immersed, heating means for heating the liquid, means for forcibly circulating the liquid, a temperature sensor for measuring the temperature of the liquid, and controlling means for controlling the heating means based on the temperature measured by the temperature sensor, whereby when the affected area is immersed in the liquid having a controlled temperature, the body temperature in a deep region is increased so that thermotherapeutic permeation effect achieved. (Patent Document 3). These apparatuses are, however, large in size and expensive.

As described in the foregoing, the conventionally known methods for externally treating *tinea* unguium are not very effective. There are no external medicines for treating *tinea* unguium which are admitted by the Ministry of Health, Labor and Welfare, Japan. Further, only a few kinds of oral medicines are admitted by the Ministry of Health, Labor and Welfare, Japan for use in clinical sites for the treatment of *tinea* unguium. The present applicant has filed an application for a patent pertaining to a device for treating *tinea* unguium which device is to solve the aforementioned problems and which device can permit an antifungal agent for external use to efficiently penetrate into a deep part of the nail by applying, to a surface of the nail infected with *Trichophyton*, a liquid of the antifungal agent for external use dissolved in a solvent (Japanese patent application No. 2008-292958).

The present invention includes the above invention.

PRIOR ART DOCUMENTS

Patent Document

Patent Document 1: Japanese published unexamined patent application No. 2004-135954
Patent Document 2: Japanese published unexamined patent application No. 2006-75357
Patent Document 3: Japanese published unexamined patent application No. 2003-126136

SUMMARY OF THE INVENTION

Problems to be Solved by the Invention

Among methods for the treatment of *tinea* unguium, the conventional method in which a liquid antifungal agent for external use is applied to a surface of the nail cannot allow penetration of thereof into a deep part of the nail because the solvent is readily evaporated so that the viscosity thereof increases. On the other hand, a method in which an antifungal agent is orally administered is not freely applicable to patients with basic diseases, such as liver diseases, pregnant women or lactating patients. Additionally, particular care with respect to concomitant administration must be given to patients who are taking other medicines. The present invention is contemplated to solve various problems of the conventional *tinea* unguium treatment methods and to provide a safe device which is capable of treating *tinea* unguium within a short period of time without causing any side effect or any interindividual difference in treatment effect.

Means for Solving the Problems

In solution of the above-described problems, the first to third aspects of the present invention provide a device for treating *tinea* unguium of nail, comprising a dome-shaped applicator formed of an elastic material and having a feed port, provided with a backflow preventing mechanism, for feeding an antifungal agent for external use, wherein the dome-shaped applicator has an open part and a flange which is provided along a periphery of the open part and which is configured to be hermetically bonded to the nail.

In accordance with a fourth aspect of the invention, there is provided a device for treating *tinea* unguium of nail, comprising a dome-shaped applicator formed of an elastic material and having a predetermined portion that is inflatable when an antifungal agent for external use is fed under pressure, wherein the dome-shaped applicator has an open part and a flange which is provided along a periphery of the open part and which is configured to be hermetically bonded to the nail.

Fifth to seventh aspects of the invention provide the above-described devices for treating *tinea* unguium of nail, wherein the inflatable portion of the dome-shaped applicator has a structure which is made from a thin film at an upper part or a side part thereof.

An eighth aspect of the invention provides the above-described devices for treating *tinea* unguium of nail, wherein the thin film portion of the dome-shaped applicator which is to be inflated upon an increase of inside pressure by feeding the antifungal agent for external use under pressure is reinforced by a thick film.

A ninth aspect of the invention provides the above-described devices for treating *tinea* unguium of nail, wherein the dome-shaped applicator has a side portion that has a bellows structure with extension and contraction property.

A tenth aspect of the invention provides the above-described devices for treating *tinea* unguium of nail, wherein the dome-shaped applicator formed of an elastic material and has a concave portion that is invertible outward when the inside pressure is increased as a result of the feeding of an antifungal agent for external use under pressure, and wherein the dome-shaped applicator has a flange which is provided along a periphery of an open part and which is configured to be bonded to the nail.

An eleventh aspect of the invention provides the above-described device for treating *tinea* unguium of nail, wherein a portion that surrounds the concave portion, which is invertible outward when an antifungal agent for external use is fed under pressure, is made from a thick film.

Effect of the Invention

As a method for treating *tinea* unguium, there have been conventionally mainly adopted a method in which a liquid antifungal agent for external use is applied to a surface of the nail and a method in which an antifungal agent is orally administered. These methods, however, are not efficient. Further, patients capable of being treated by these methods are limited. On the other hand, a method in which a dome-shaped applicator according to the present invention is used is effectively applicable to patients with basic diseases, such as liver diseases, pregnant women and lactating patients and, additionally, gives an excellent effect that the antifungal agent for external use is allowed to penetrate to a deep part of a nail infected with *Trichophyton* by merely maintaining the dome-shaped applicator which contains a liquid antifungal agent for external use to be hermetically bonded to a surface of the nail for one to several days.

According to the first to third aspects of the invention of the present application which provide a device for treating *tinea* unguium of nail that comprises a dome-shaped applicator having a feed port, provided with a backflow preventing mechanism, for feeding an antifungal agent for external use, and a flange which is provided along a periphery of an open part and which is configured to be bonded to the nail, it is possible to solve the problem of the conventional method in which a liquid antifungal agent for external use is applied to a surface of the nail. Namely, by merely maintaining the device to be bonded to a surface of the nail for one to several days, the problem of the conventional method that the antifungal agent for external use fails to penetrate into a deep part of the nail due to quick evaporation of the solvent can be solved. Moreover, it is possible to treat patients with basic diseases, such as liver diseases, pregnant women and lactating patients, who are prohibited from administering oral medicines.

According to the above-described fourth to seventh aspects of the invention in which the dome-shaped applicator has a predetermined portion that is inflatable when an antifungal agent for external use is fed under pressure, it is possible to control the inside pressure by feeding the antifungal agent for external use under pressure so as to inflate the predetermined portion. Additionally, it is possible to allow the antifungal agent for external use to efficiently penetrate into a deep part of a nail infected with *Trichophyton* by maintaining the inside space at positive pressure.

According to the above-described eighth aspect of the invention in which an inflatable thin film part of the dome-shaped applicator is reinforced by a thick film, it is possible to prevent deformation of the dome-shaped applicator and to prevent separation between the flange, provided along a periphery of the open part, and the nail.

According to the above-described ninth aspect of the invention in which the dome-shaped applicator has a side wall portion that has an bellows structure, it is possible to allow the antifungal agent for external use to efficiently penetrate into a deep part of a nail by utilizing the force that urges the bellows structure, inflated by the feeding of the antifungal agent for external use under pressure, to return to its original shape.

According to the above-described tenth aspect of the invention in which the dome-shaped applicator is formed with a concave portion that is movable outward and inward depending upon the pressure inside thereof, it is possible to allow the antifungal agent for external use to efficiently penetrate into a deep part of a nail by utilizing the force that urges the concave portion, moved outward by an increase of the inside pressure upon feeding of the antifungal agent for external use under pressure, to return to its original shape.

According to the above-described eleventh aspect of the invention providing a device for treating *tinea* unguium of a nail in which a portion surrounding the concave portion, that is invertible outward by an increase of the inside pressure, is reinforced by a thick film, it is possible to allow the concave portion to be efficiently inverted.

EMBODIMENTS FOR CARRYING OUT THE INVENTION

Figure 1:
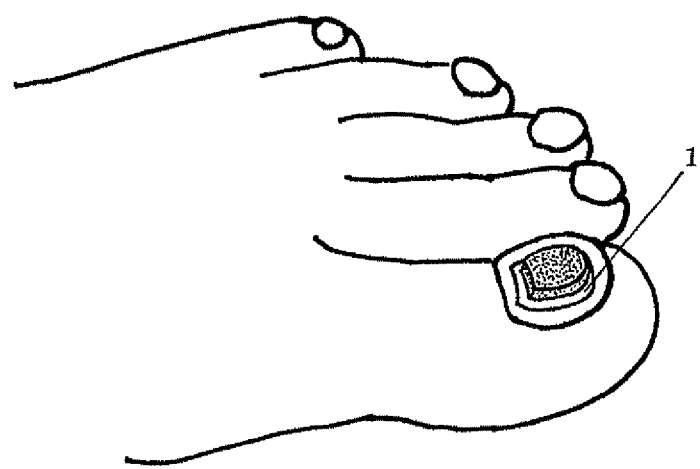
FIG. 1 is a perspective view illustrating the state in which a dome-shaped applicator is hermetically bonded to a surface of a nail.

The gist of the present invention resides in that an antifungal agent for external use efficiently penetrates deep into a *Trichophyton*-infected nail by hermetically bonding a dome-shaped applicator, into which the antifungal agent for external use has been injected, to a surface of the nail. In the present specification, the device for treating *tinea* unguium is described as comprising a dome-shaped applicator. However, the shape of the *tinea* unguium treating device according to the present invention is not limited only to a "dome-shaped" form such as often seen in all weather sport facilities but may be in any form having a structure, such as a circular cylinder, an elliptical cylinder, a polygonal cylinder, a finger cot, a but or a bowl, that has an open portion which is configured to contact with a *Trichophyton*-infected nail and a flange portion which is provided along a periphery of the open part and which is configured to be hermetically bonded to the nail so as to prevent the liquid antifungal agent for external use from leaking therethrough.

A nail to be treated by the technology according to the present invention has a hard tissue composed of walls of superposed bricks of keratin which is a protein and does not have sebaceous gland or sweat gland. Therefore, neither sweat nor sebum which might act as the solvent is secreted from the nail. Moreover, the nail has a three-layered structure in which the outermost surface layer is hard. When a liquid antifungal agent for external use is applied to the nail, the solvent is evaporated before the antifungal agent for external use penetrates from the surface of the nail into a deep part thereof. With such a method, therefore, it has been considered to be impossible to make a sufficient amount of the antifungal agent penetrate into a deep part of the *Trichophyton*-infected nail. The present invention has enabled to allow a sufficient amount of an antifungal agent for external use to penetrate deep into a *Trichophyton*-infected nail by hermetically adhering a dome-shaped applicator, into which the antifungal agent for external use has been injected, to a surface of the nail.

The configuration of the dome-shaped applicator suitably used for the purpose of the present invention may be roughly divided into three types, each of which is described below.

It is preferred that the dome-shaped applicator suitably used in the present invention be molded of a material having good flexibility and elasticity irrespective of the type thereof. A rubber material such as a polybutadiene-based rubber, a butadiene-acrylonitrile-based rubber, a chloroprene-based rubber, an acryl rubber, an acrylonitrile-butadiene rubber, an isoprene rubber, an urethane rubber, an ethylene-propylene rubber, an epichlorohydrin rubber, a chloroprene rubber, a silicone rubber, a styrene-butadiene rubber, a butadiene rubber, a fluorine rubber and a polyisobutyrene rubber may be suitably used. Particularly preferred is a butyl rubber since rupture upon insertion of a needle of an injector can be surely avoided and since compatibility thereof with various adhesive agents is good.

Each type of the dome-shaped applicators according to the present invention is described below with reference to the drawings.

Figure 2:
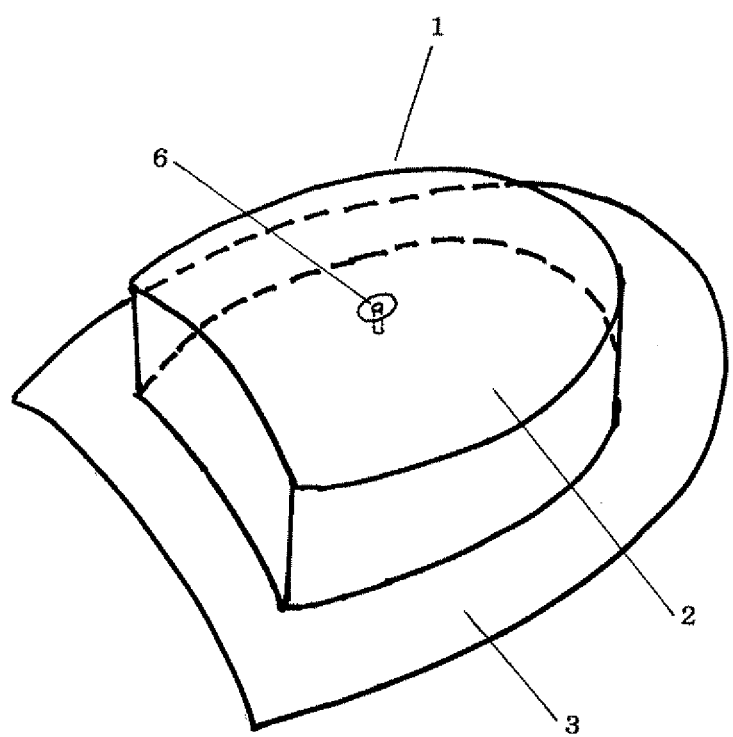
FIG. 2 shows a dome-shaped applicator of a first type.

At the outset, the first type of the dome-shaped applicator is described with reference to FIG. 1 which schematically depicts the dome-shaped applicator 1 of the present invention in the state where it is mounted to a foot nail. FIG. 2 shows the typical dome-shaped applicator 1 of the first type as a perspective view. The dome-shaped applicator 1 of the first type has a fluid feed port 6 which is provided with a backflow preventing mechanism, and a flange 3 which is provided along a periphery of an open part and which has an adhesive layer for hermetically bonding the applicator to the nail. After the typical dome-shaped applicator 1 has been hermetically bonded to a surface of the nail, an antifungal agent for external use is injected, through the fluid feed port 6 provided with a backflow preventing mechanism, into an inside space 2 defined in the dome-shaped applicator 1 using a suitable injector such as a syringe. The fluid feed port 6 provided with a backflow preventing mechanism may have any known mechanism such as those utilized in tennis balls and are not specifically limited.

Figure 3A:
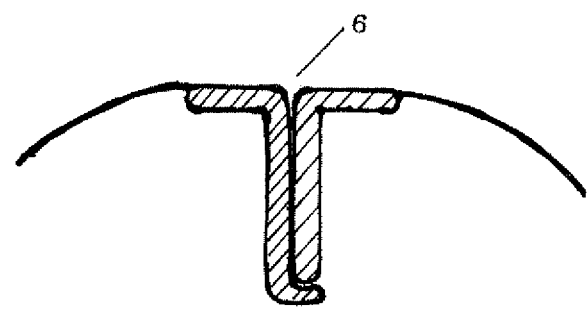
FIG. 3 is enlarged schematic illustrations of fluid feed ports.

Typical structures of the fluid feed port 6 provided with a backflow preventing mechanism are schematically illustrated in FIGS. 3(A) and (B). It is without saying that other structures may also be used.

There are often cases where it is difficult to attain hermetical adhesion because of non-flatness of a surface of the *Trichophyton*-infected nail. Thus, when the adhesive agent provided on the flange 3 alone fails to provide a sufficient adhesion strength, it is necessary to strengthen the adhesion using an adhesive tape, etc.

According to the present invention, it is possible to allow a liquid antifungal agent for external use to penetrate to a deep part of the nail by merely hermetically bonding the dome-shaped applicator which contains the liquid antifungal agent for external use to a surface of the nail without evaporation or leakage of the solvent of the liquid antifungal agent for external use.

Figure 4:
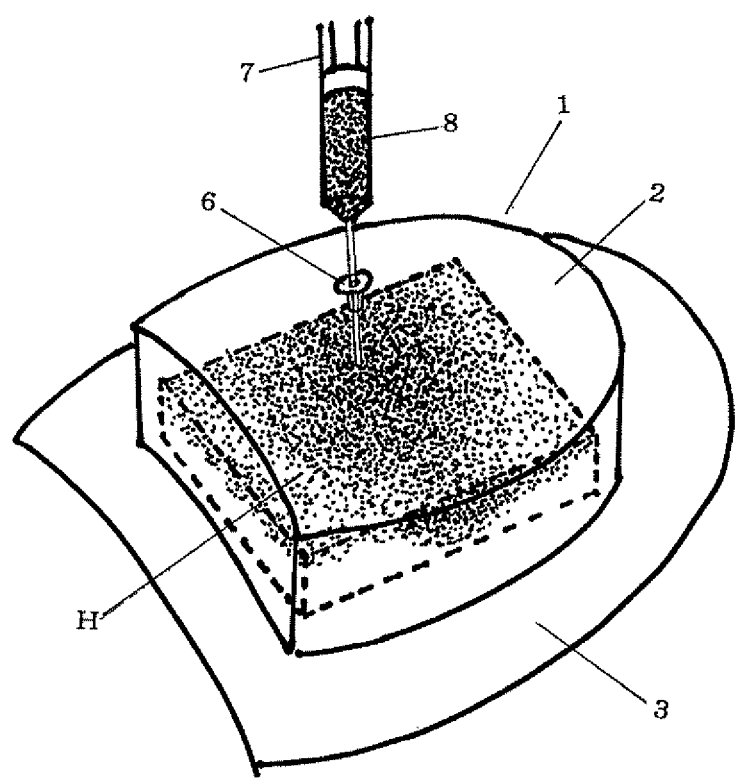
FIG. 4 shows another embodiment of the dome-shaped applicator of the first type.

FIG. 4 shows an embodiment of the dome-shaped applicator 1 in which a liquid antifungal agent for external use is injected in the state where a retaining member H is provided inside the dome-shaped applicator 1 for retaining the antifungal agent for external use. Preferred examples of the retaining member H include a filter paper, a non-woven fabric, a polymeric absorbent material and a sponge with an open cells, which have good water retaining property.

After the dome-shaped applicator 1 provided inside with the retaining member H has been hermetically bonded to a surface of the nail, an antifungal agent 8 for external use is injected through the fluid feed port 6 provided with a backflow preventing mechanism using a suitable injector 7 such as a syringe. By previously proving the retaining member H inside the dome-shaped applicator 1, the liquid antifungal agent 8 for external use does not readily escape therefrom even when the bonded area of the dome-shaped applicator 1 is partly debonded due to a movement thereof during use.

Figure 3B:
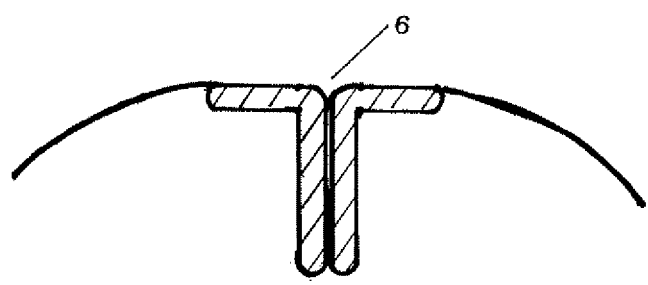
Figure 5:
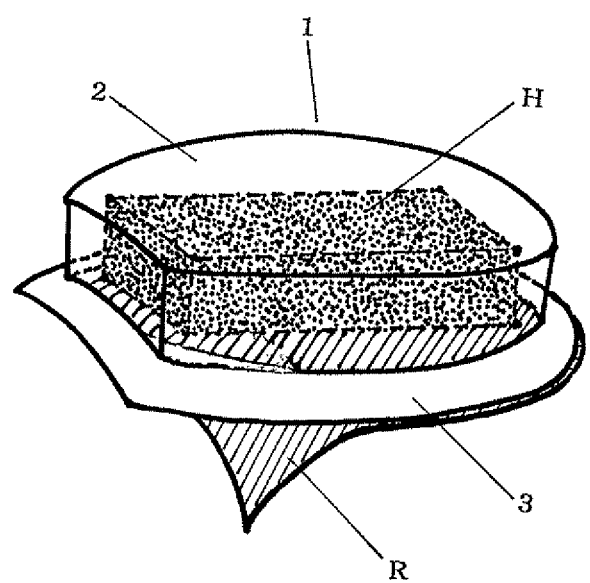
FIG. 5 shows a further embodiment of the dome-shaped applicator of the first type.

FIG. 5 shows a further embodiment of the dome-shaped applicator 1 of the first type and depicts the state in which the dome-shaped applicator 1 is filled with a retaining member H previously impregnated with a solution of an antifungal agent for external use and in which a release sheet R is provided at the bottom open part thereof for preventing the solvent from evaporating therefrom. At the time the dome-shaped applicator 1 of this type is bonded to a surface of a nail, it is necessary to peel and remove the release sheet R. The dome-shaped applicator 1 may be readily used by merely peeling off the release sheet R. Except for the necessity of peeling, the dome-shaped applicator 1 is the same as that shown in FIGS. 2 and 3. In the embodiment shown in FIG. 5, it is not particularly necessary to provide a fluid feed port having a backflow preventing mechanism, because the retaining member H previously impregnated with an antifungal agent for external use is filled and hermetically accommodated in the dome-shaped applicator 1. Such a fluid feed port, however, may be provided for the purpose of injecting an antifungal agent for external use again.

Figure 6:
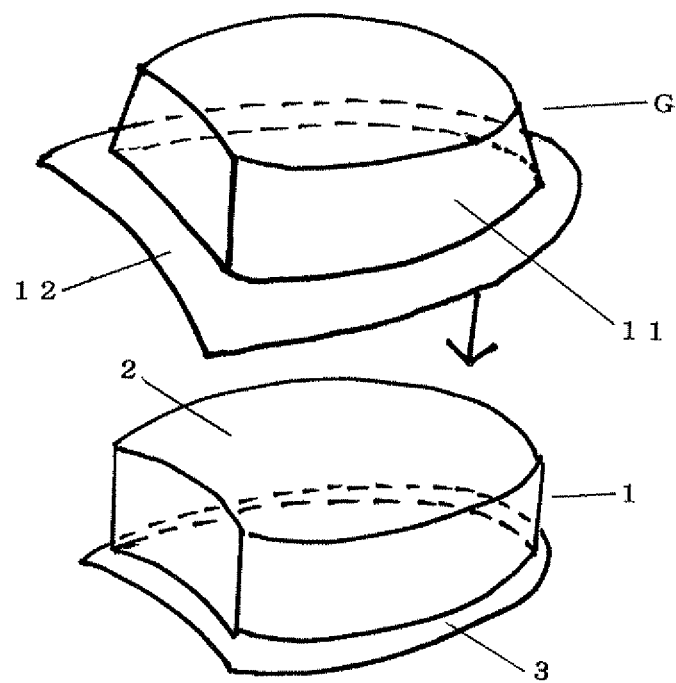
FIG. 6 shows an embodiment of use of the dome-shaped applicator of the first type.
Figure 6:
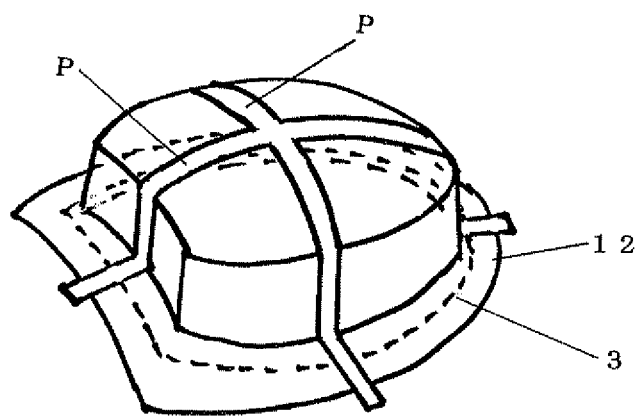

As described above, the present invention enables to allow an antifungal agent for external use to penetrate deep into a nail by merely hermetically bonding a dome-shaped applicator, into which the antifungal agent for external use has been filled, to a surface of the nail. The penetration of the antifungal agent for external use into the nail may be more surely attained by a method as shown in FIG. 6, in which the dome-shaped applicator 1 is first covered with and pressed by an outer cover G having a smaller diameter than that of the dome-shaped applicator which has been hermetically bonded to a surface of the nail. The assembly is then fixed under tension by a fixing member P such as an adhesive tape so that the inside space of the dome-shaped applicator 1 is forcedly maintained in a positive pressure. As a consequence, the antifungal agent for external use is allowed to penetrate into a deep part of the nail.

The second type of the dome-shaped applicator is next described. The dome-shaped applicator of the second type has a thick film portion and a thin film portion. A liquid antifungal agent for external use is injected through the thick film portion using an injector such as a syringe. Since the dome-shaped applicator is formed of a material having good flexibility and elasticity, the pinhole formed with a needle of the injector is spontaneously closed. When the liquid antifungal agent for external use is injected through the thick film portion using an injector such as a syringe, a positive pressure is established in the inside of the dome-shaped applicator so that the antifungal agent for external use is allowed to positively penetrate into a deep part of the nail. A the same time, the thin film portion of the dome-shaped applicator inflates as a balloon as a result of an increase of the inside pressure. Thus, the above configuration of the dome-shaped applicator also serves to control the inside pressure thereof. The dome-shaped applicator of the second type is not formed throughout of a thin film. Rather, a lower part of the dome-shaped applicator is formed of the thick film. Because the lower part is formed of the thick film, the shape of the dome-shaped applicator is stabilized so that, even when the dome-shaped applicator is deformed due to a movement thereof, a flange 3 is prevented from debonding from a surface of the nail.

Figure 7:
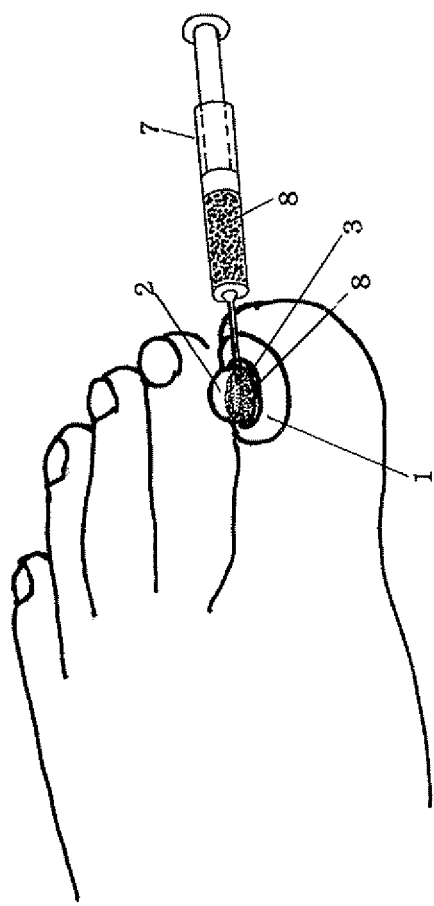
FIG. 7 shows a dome-shaped applicator of a second type.

FIG. 7 is a perspective view of a dome-shaped applicator 1 of the second type in the state where an antifungal agent 8 for external use is being injected using an injector 7. In order that the antifungal agent for external use can be injected into the dome-shaped applicator, it is necessary for a pinhole formed by a needle of the injector to be spontaneously closed. In order for the pinhole to be spontaneously closed, it is not only necessary that the applicator should be formed of a material having good flexibility and elasticity but also that the antifungal agent for external use should be injected at the thick film portion.

More particularly, as shown in the perspective view of FIG. 7, it is preferred that the antifungal agent for external use be injected by inserting the needle of the injector 7 through the thick film portion in parallel with the nail surface. This is because, if antifungal agent for external use is injected into the dome-shaped applicator 1 from upward using the injector 7, there is a danger that the needle may penetrate through the nail into the skin. In one embodiment of use of the dome-shaped applicator of the second type, the dome-shaped applicator is hermetically bonded to a surface of the nail. Thereafter, the antifungal agent 8 for external use is injected using a suitable injector 7 to inflate the thin film portion and to establish a positive pressure within the dome-shaped applicator 1. By this, the antifungal agent 8 for external use can efficiently penetrate into a deep part of the nail.

Figure 8:
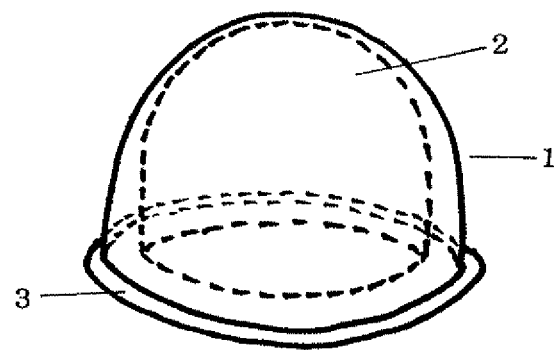
FIG. 8 shows a dome-shaped applicator of the second type.

FIG. 8 to FIG. 13 illustrate various embodiments of the dome-shaped applicator of the second type according to the present invention. FIG. 8 shows a typical dome-shaped applicator of the second type according to the present invention in a perspective view. As shown in FIG. 8 which is an enlarged schematic illustration, the dome-shaped applicator 1 is characterized in that a lower part of its inside space 2 is defined by a thick film while an upper part of its inside space 2 is defined by a thin film capable of being inflated by an increase of the pressure thereof upon injection of an antifungal agent for external use thereinto. The dome-shaped applicator 1 has a flange 3 provided in an open end thereof. The flange 3 may have a coating of an adhesive agent and a release member covering the coating. In lieu of the method in which the adhesive agent is coated and the coating is covered with the release member, it is possible to use an instantaneous adhesive agent for rapid bonding.

Figure 9:
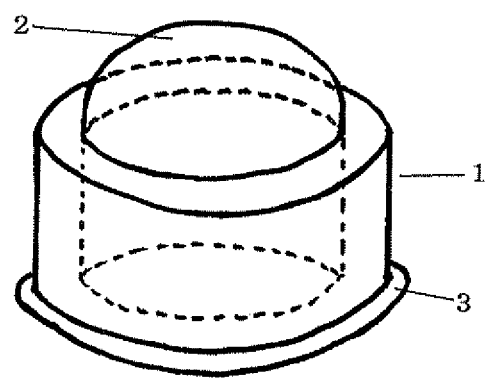
FIG. 9 shows another embodiment of the dome-shaped applicator of the second type.

Irrespective of the embodiments the dome-shaped applicator 1 according to the present invention, it is necessary that the dome-shaped applicator should be formed of a material having good flexibility and elasticity in order that a hole is spontaneously closed after the extraction of a needle of an injector without being applied with a seal material. FIG. 9 shows another configuration of the dome-shaped applicator 1 of the second type. In the dome-shaped applicator shown in FIG. 8, the thickness of the film is gradually reduced from the open part thereof toward the upper part thereof. In the dome-shaped applicator shown in FIG. 9, on the other hand, the thick film portion and thin film portion are clearly distinct. Namely, the lower part of the dome-shaped applicator 1 is like a ring of a thick film and has a configuration to maintain its stability even when the applicator is subjected to an intense motion.

FIG. 8 and FIG. 9 each show a typical dome-shaped applicator 1 of the second type according to the present invention. The dome-shaped applicator 1 of the present invention is, however, not limited to a round shape as illustrated in FIG. 8 and FIG. 9 and may be in an ellipsoidal shape or in any other shape corresponding to the surface shape of the nail. The thickness of the film is not specifically limited as long as the applicator can be stably bonded to a surface of the nail and a hole formed by a needle of an injector is closed.

Figure 10:
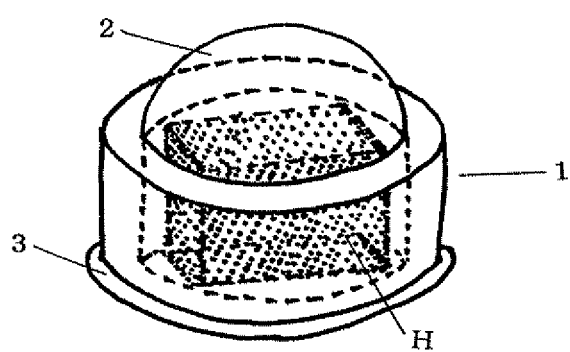
FIG. 10 shows a further embodiment of the dome-shaped applicator of the second type.

FIG. 10 shows an embodiment of the dome-shaped applicator 1 in which a porous retaining member H such as a filter paper, a non-woven fabric, a polymeric absorbent material or a sponge, which is capable of absorbing an antifungal agent for external use, is provided. By proving such a material capable of absorbing an antifungal agent for external use inside the dome-shaped applicator 1, even when the dome-shaped applicator 1 is debonded from the nail due to some reason, the liquid antifungal agent for external use does not readily escape therefrom and is retained therein.

Figure 11:
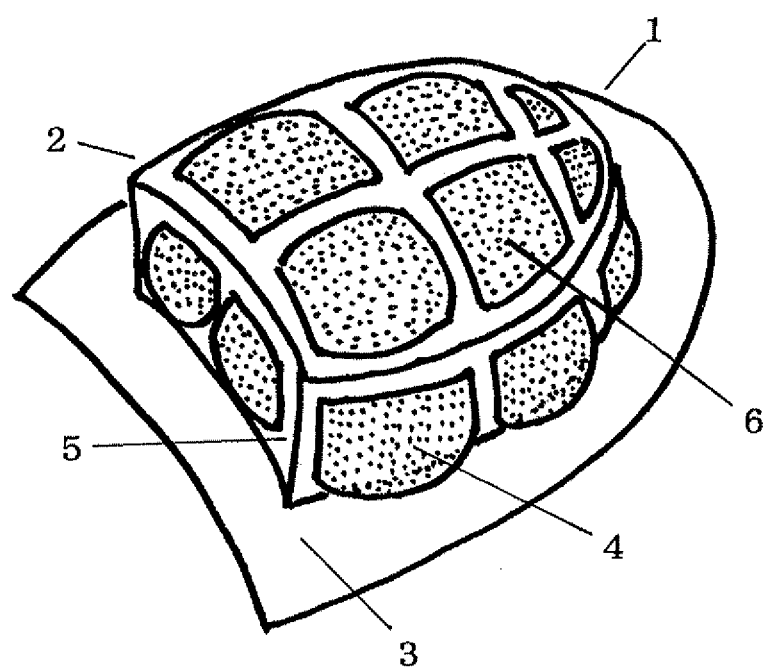
FIG. 11 shows a further embodiment of the dome-shaped applicator of the second type.
Figure 12A:
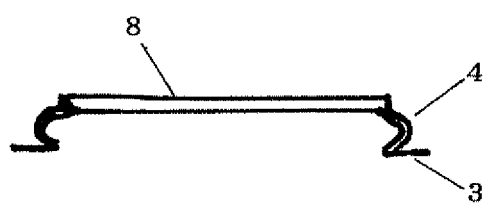
FIG. 12 shows a further embodiment of the dome-shaped applicator of the second type.
Figure 12B:
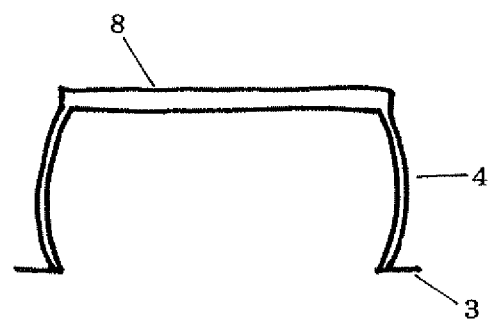
Figure 13A:
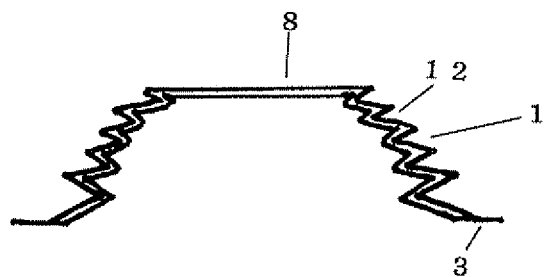
FIG. 13 shows a further embodiment of the dome-shaped applicator of the second type.
Figure 13B:
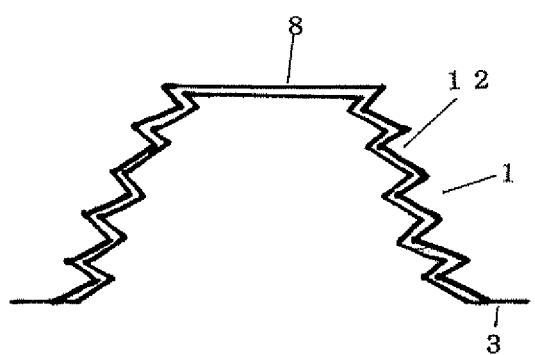

FIG. 11 is a perspective view of a modified dome-shaped applicator of the second type. The dome-shaped applicator of the second type is characterized in that the thin film portion is inflated by an increased pressure upon injection of an antifungal agent for external use. In this embodiment, a reinforcing member 5 formed of a thick film of a grid-like form is provided for the purpose of preventing the dome-shaped applicator from becoming unstable due to excessive deformation thereof upon inflation of the thin film portion. Since deformation of the dome-shaped applicator 1 by inflation is suppressed by the reinforcing member 5 formed of a thick film, the shape of the dome-shaped applicator 1 is retained.

The dome-shaped applicator 1 of the second type which uses inflation and deflation thereof by injection of the antifungal agent for external use thereinto may be embodied in other various forms. For example, the applicator shown in FIG. 12 has a top portion formed of a thick film and a side portion formed of a thin film and is originally in the form as shown in (A). When the inside pressure of the applicator is increased as a result of the injection of the antifungal agent for external use thereinto, the applicator takes the form as shown in (B). The antifungal agent for external use is thus pressurized and penetrates in a deep portion of the nail and, after that, returns against to the state as shown in (A). The dome-shaped applicator 1 shown in FIG. 13 utilizes the same principle as above but differs from that shown in FIG. 12 in that a bellows structure 12 is used in the side portion in place of the thin film. The bellows structure 12 in the side portion is normally in a retracted state so that an antifungal agent for external use within the dome-shaped applicator is urged to flow out.

In the various embodiments of the dome-shaped applicator according to the present invention, the thickness of the thick film portion and the thin film portion is not specifically limited. However, the thickness of the thick film portion is preferably in the range of 2 mm to 5 mm, while the thickness of the thin film portion is preferably in the range of 0.02 mm to 2 mm.

The third type of the dome-shaped applicator is next described. In the above-described dome-shaped applicator of the second type, the thin film formed in an upper part thereof is inflated like a balloon by injection of the antifungal agent for external use so that the antifungal agent for external use efficiently penetrates into a deep part of the nail with the inside pressure thereof being controlled. In the dome-shaped applicator of the third type, the flexibility and elasticity of the material of which the applicator is formed are utilized such that a concave portion provided at a predetermined position thereof is inverted outward by an increase of the inside pressure caused when an antifungal agent for external use is injected into the applicator. Even when the concave portion has been deformed outward by the inside pressure, the concave portion always tends to return to the original shape. Therefore, the antifungal agent for external use is positively urged to penetrate into a deep part of the nail. Thus, the dome-shaped applicator of the third type is contemplated to allow the antifungal agent for external use to penetrate into a deep part of the nail by utilizing the repulsive force of its concave portion to return to the original shape. While various configurations may be considered theoretically for the dome-shaped applicator of the third type, concrete description will be made below of embodiments with reference to FIG. 14 to FIG. 18 which are considered by experience to be particularly preferred.

The third type of the dome-shaped applicator is described with reference to the perspective view of FIG. 14, wherein (A) shows the typical dome-shaped applicator of the third type which is provided with a concave portion formed by depressing a top dome-like portion made of an elastic material and which has a shape resembling the shape of a finger cot made of a rubber and having its end portion depressed; (B) shows the state of the dome-shaped applicator in which an antifungal agent for external use is being injected thereinto using an injector such as syringe; and (C) shows the state in which the injection of the antifungal agent for external use has been completed so that the concave portion formed in the top of the dome-shaped applicator has been inverted outward by an increase of the inside pressure. In this case, since the concave portion formed in the top of the dome-shaped applicator always tends to return to the original shape, the antifungal agent for external use is applied with a positive pressure.

Figure 14A:
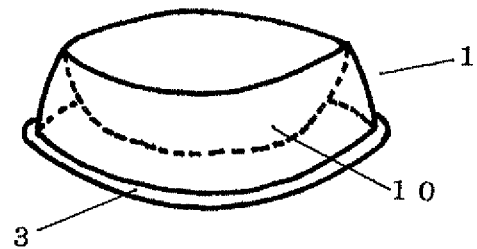
FIG. 14 shows a dome-shaped applicator of a third type.

The perspective views of FIGS. 14(A), (B) and (C) are specifically described next. A flange 3 of the dome-shaped applicator 1 is bonded to a surface of a nail infected with *Trichophyton*. An antifungal agent 8 for external use is then injected using an injector 7 such as a syringe, whereupon the inside pressure is increased so that a concave portion 10 in a top portion of the dome-shaped applicator 1 is inverted outward at a folding portion 9. Since the dome-shaped applicator 1 is formed of an elastic material and the concave portion 10 tends to return to the original shape, the inside of the dome-shaped applicator 1 is always maintained in a positive pressure environment. Thus, the antifungal agent 8 for external use is allowed to penetrate into a deep part of the nail.

Figure 14B:
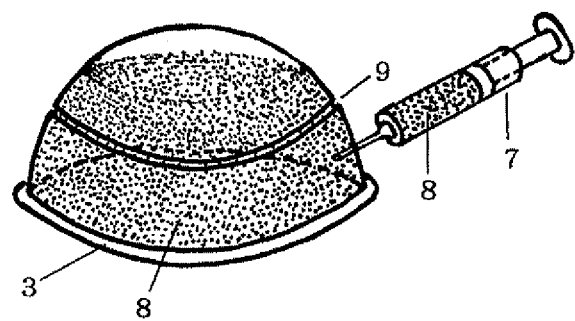
Figure 14C:
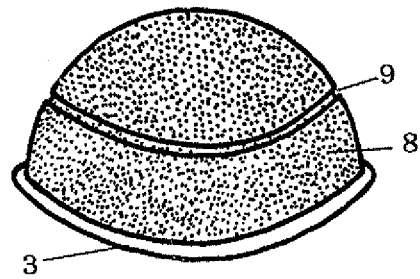
Figure 15A:
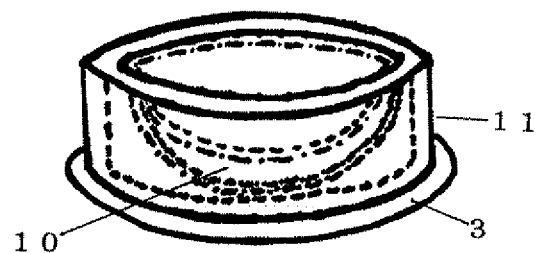
FIG. 15 shows another embodiment of the dome-shaped applicator of the third type.
Figure 15B:
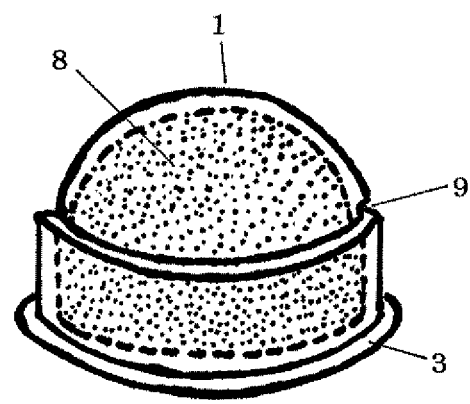
Figure 16:
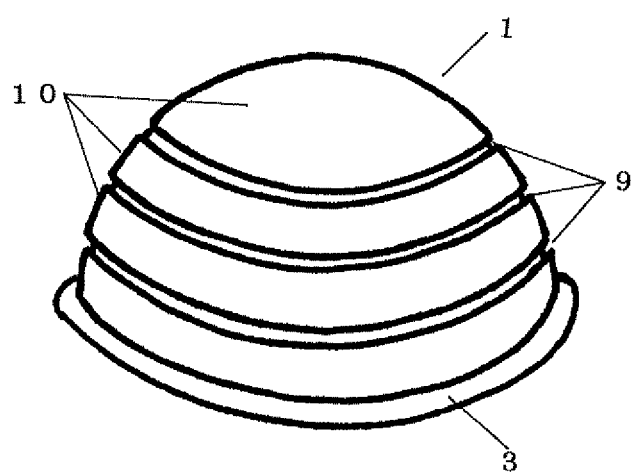
FIG. 16 shows a further embodiment of the dome-shaped applicator of the third type.

The dome-shaped applicator 1 shown in FIG. 15 is basically the same as that shown in FIG. 14 but slightly differs therefrom in configuration. Namely, they are the same with each other in that the concave portion 10 is formed in a top portion of the dome-shaped applicator 1. The dome-shaped applicator 1 shown in FIG. 15, however, has a lower part 11 formed of a cylindrical thick film. Therefore, the simple device for treating *tinea* unguium has improved strength. The antifungal agent for external use may be easily injected through the thick film portion using an injector. FIG. 15(A) illustrates the state before injection of the antifungal agent for external use, while FIG. 15(B) illustrates the state after the antifungal agent for external use has been injected. It is preferred that the dome-shaped applicator 1 have a folding portion 9 at a boundary between the cylindrical portion 11 and the concave portion 10, as shown in FIGS. 15(A) and (B). In the embodiment shown in FIGS. 15(A) and (B), there is only one folding portion 9. It is possible, however, that a plurality of folding portions 9 are formed as shown in FIG. 16. Typical configurations of the dome-shaped applicator of the third type according to the present invention have been described above for the purpose of easy understanding. Various other configurations of the dome-shaped applicator of the third type may be thought of.

Figure 17:
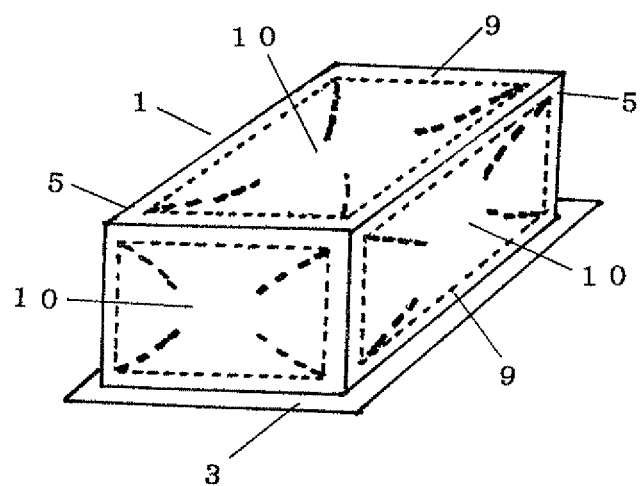
FIG. 17 shows a further embodiment of the dome-shaped applicator of the third type.
Figure 18:
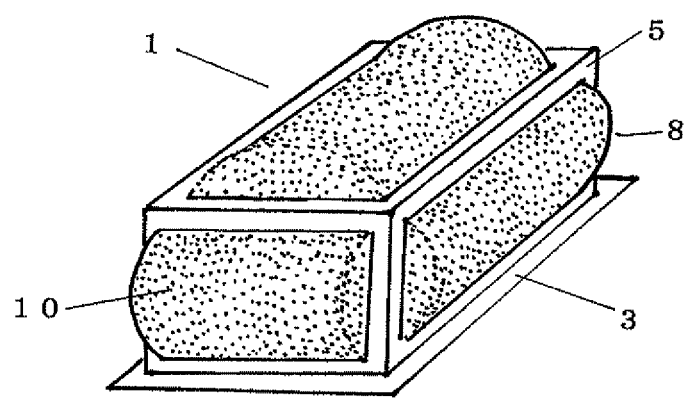
FIG. 18 shows a further embodiment of the dome-shaped applicator of the third type.

For example, as shown in FIG. 17, a cubic form corresponding to the shape of the nail may be thought of as an example of other configurations. The dome-shaped applicator 1 schematically shown in FIG. 17 might be considered as being quite different from those shown in FIGS. 14 to 16 but is not substantially different from those shown in FIGS. 14 to 16. In the dome-shaped applicator shown in FIG. 17, a portion corresponding to the concave portion formed by depressing the top of the dome-shaped applicator of FIGS. 14 to 16 is provided in each of the four circumferential sides and the top side thereof (i.e. five sides in total). Further, a reinforcing member 5 formed of a thick film is provided in each folding portion 9 of the dome-shaped applicator 1. FIG. 18 illustrates the above dome-shaped applicator in the state in which it is bonded to a surface of a nail and the liquid antifungal agent 8 for external use is injected thereinto so that each of the concave portions 10 is inverted outward. The dome-shaped applicator 1, in which the liquid antifungal agent 8 for external use has been injected and the concave portions 10 has been inverted outward as shown in FIG. 18, is of course returned to the state shown in FIG. 17 when the inside pressure is reduced as a result of the penetration of the liquid antifungal agent 8 for external use into a deep part of the nail.

EXAMPLES

Example 1

The dome-shaped applicator of the first type as shown in FIG. 2 (inside volume: 0.15 mL) was used. A commercially available instantaneous adhesive agent (cyanoacrylate-based adhesive) was applied to the flange of the applicator for bonding. The flange was then hermetically bonded to a surface of a nail. Using a syringe (inside volume: 0.5 mL), 0.15 mL of a solution having a terbinafine hydrochloride content of 1% was injected through the feed port. The feed port was then opened so that the inside and outside of the applicator was in fluid communication with each other. Thus, the inside air was released and the inside of the dome-shaped applicator reached ambient pressure (1.0 atm.). The applicator was maintained as such for two days and then removed from the nail. A part of the tip of the nail was cut and measured for the concentration of the terbinafine hydrochloride. The measured terbinafine hydrochloride content in the nail is shown in Table for Comparison below.

Example 2

The dome-shaped applicator of the second type as shown in FIG. 8 (inside volume: 0.15 mL) was used. A commercially available instantaneous adhesive agent (cyanoacrylate-based adhesive) was applied to the flange of the applicator for bonding. The flange was then hermetically bonded to a surface of a nail. Using a syringe (inside volume: 0.5 mL), 0.15 mL of a solution having a terbinafine hydrochloride content of 1% was injected through the thick film portion near the opening of the dome-shaped applicator.

Because the dome-shaped applicator was hermetically bonded to the nail, the thin film portion in the upper part thereof inflated. The inside pressure of the dome-shaped applicator was measured and found to be 1.3 atm, indicating that the pressure was increased by 0.3 atm from the ambient pressure. The dome-shaped applicator was maintained in the hermetically bonded state for two days and then removed from the nail. A part of the tip of the nail was cut and measured for the concentration of the terbinafine hydrochloride. The measured terbinafine hydrochloride content in the nail is shown in Table for Comparison below.

Example 3

The dome-shaped applicator of the third type as shown in FIG. 15 (inside volume: 0.15 ml.) was used. A commercially available instantaneous adhesive agent (cyanoacrylate-based adhesive) was applied to the flange of the applicator for bonding. The flange was then hermetically bonded to a surface of a nail. Using a syringe (inside volume: 0.5 mL), 0.15 mL of a solution having a terbinafine hydrochloride content of 1% was injected through the thick film portion near the opening of the dome-shaped applicator. Because the dome-shaped applicator was hermetically bonded to the nail, the thin film portion in the upper part thereof was inverted and protruded as shown in FIG. 15(B). The inside pressure of the dome-shaped applicator was measured and found to be 1.3 atm, indicating that the pressure was increased by 0.3 atm from the ambient pressure.

The dome-shaped applicator was maintained in the hermetically bonded state for two days and then removed from the nail. A part of the tip of the nail was cut and measured for the concentration of the terbinafine hydrochloride. The measured terbinafine hydrochloride content in the nail is shown in Table for Comparison below.

Comparative Example 1

As conventionally used as a treatment method for *tinea* unguium, a terbinafine hydrochloride tablet was orally administered once a day continuously for 4 weeks. A part of the tip of the nail was then cut and measured for the concentration of the terbinafine hydrochloride in the same manner as in Examples 1 to 3. The measured terbinafine hydrochloride content in the nail is shown in Table for Comparison below.

Table for Comparison

|  | Example 1 | Example 2 | Example 3 | Comparative Example 1 |
|---|---|---|---|---|
| No. 1 | 27.0 | 43.7 | 41.5 | 0.24 |
| No. 2 | 40.8 | 66.1 | 67.2 | 0.38 |
| No. 3 | 67.6 | 88.8 | 86.3 | 0.15 |
| No. 4 | 42.9 | 68.6 | 70.2 | 0.28 |
| No. 5 | 52.0 | 104.9 | 75.8 | 0.45 |
| No. 6 | 32.4 | 38.9 | 42.3 | 0.11 |
| Average | 43.8 | 68.5 | 63.9 | 0.38 | ng/mg

Incidentally, a 1% terbinafine hydrochloride external medicine was applied to a surface of a nail twice a day continuously for 4 weeks. A part of the tip of the nail was then cut and measured for the concentration of the terbinafine hydrochloride. Almost no terbinafine hydrochloride was detected in a deep part of the nail, though the terbinafine hydrochloride was found to slightly penetrate into a surface region of the nail.

In Comparative Example 1, the measurement of terbinafine hydrochloride was carried out after administration period of 4 weeks, because the terbinafine hydrochloride was not detected after administration of 2 days.

It is evident from the results shown in above Table for Comparison that terbinafine hydrochloride transdermally penetrates into the nail with the use of the simple device for treating *tinea* unguium according to the present invention.

INDUSTRIAL APPLICABILITY

The simple dome-shaped applicator is capable of allowing an antifungal agent for external use to be efficiently absorbed from a surface of a nail to a deep part of the nail. The provision of such an applicator can make it possible to treat patients with basic diseases, such as liver diseases, pregnant women or lactating patients without any limitation. Additionally, the applicator is capable of treating at a low cost in a safe manner without causing any side effect. Therefore, it is expected that the device for treating *tinea* unguium will be widely used henceforth.

EXPLANATION OF REFERENCE NUMERALS

1: Dome-shaped applicator
2: Inside space
3: Flange
4: Thin film portion
5: Reinforcing member
6: Fluid feed port
7: Injector
8: Antifungal agent for external use
9: Folding portion
10: Concave portion
11: Lower part
12: Bellows structure
H: Retaining member
R: Release sheet
G: Outer cover
P: Fixing member

The invention claimed is:

1. A device for treating tinea unguium of nail with a liquid antifungal agent for external use supplied through a needle of an injector, comprising:

a dome-shaped applicator formed throughout of an elastic material and consisting essentially of a side wall portion defining an opening at one end thereof, an upper portion contiguous to and closing the other end of the side wall portion, and an annular flange formed along a periphery of the opening of the side wall portion and configured to be hermetically adhered to the nail, wherein said side wall portion, together with said upper portion, defines an inside space of the dome-shaped applicator, said inside space being closed when the dome-shaped applicator is attached to the nail with the annular flange being hermetically adhered to the nail, wherein the thickness of the side wall portion is such that the needle is insertible therethrough for injecting the liquid antifungal agent into the inside space but the injected liquid antifungal agent is prevented from exiting therethrough after removal of the needle therefrom, wherein the upper portion has a thin-walled portion elastically expandable outward when the antifungal agent is fed to the inside space under pressure through the needle inserted through the side wall portion, and wherein the side wall portion has a thickness in the range of 2 to 5 mm and the thin-walled portion has a thickness in the range of 0.02 to 2 mm.

2. The device as recited in claim 1, wherein the elastic material is a rubber material selected from the group consisting of a polybutadiene-based rubber, a butadiene-acrylonitrile-based rubber, a chloroprene-based rubber, an acryl rubber, an acrylonitrile-butadiene rubber, an isoprene rubber, an urethane rubber, an ethylene-propylene rubber, an epichlorohydrin rubber, a chloroprene rubber, a silicone rubber, a styrene-butadiene rubber, a butadiene rubber, a fluorine rubber, a polyisobutyrene rubber and a butyl rubber.

3. The device as recited in claim 1, further comprising an absorbent disposed within the inside space for retaining the liquid antifungal agent supplied to the inside space.

4. The device as recited in claim 1, wherein the thickness of the side wall portion gradually decreases from the periphery of the opening of the side wall portion toward the upper portion.

5. The device as recited in claim 1, wherein the thickness of the side wall portion is such that the needle is insertible therethrough but a pinhole formed in the side wall portion as a result of the insertion of the needle therethrough is spontaneously closed after removal of the needle therefrom, so that when the dome-shaped applicator is attached to the nail with the annular flange being hermetically adhered to the nail and when the needle is inserted through the side wall portion into the closed inside space under pressure and the liquid antifungal agent is injected thereinto, the closed inside space is maintained in a positive pressure after the removal of the needle from the side wall portion.

* * * * *